United States Patent [19]

Berkowitz

[11] 4,208,519

[45] Jun. 17, 1980

[54] CYANURIC ACID CHLORINATION WITH ALKALI METAL HYPOCHLORITE

[75] Inventor: Sidney Berkowitz, Highland Park, N.J.

[73] Assignee: FMC Corporation, Philadelphia, Pa.

[21] Appl. No.: 868,560

[22] Filed: Jan. 11, 1978

Related U.S. Application Data

[63] Continuation-in-part of Ser. No. 721,295, Sep. 8, 1976, abandoned.

[51] Int. Cl.$^2$ ............................................. C07D 251/36
[52] U.S. Cl. ..................................................... 544/190
[58] Field of Search ........................................ 544/190

[56] References Cited

U.S. PATENT DOCUMENTS

| | | | |
|---|---|---|---|
| 2,956,056 | 10/1960 | Christian | 544/190 |
| 3,668,204 | 6/1972 | Mesiah | 544/190 |
| 3,712,891 | 1/1973 | Berkowitz et al. | 544/190 |
| 3,806,507 | 4/1974 | Sawhill | 544/190 |
| 3,896,213 | 7/1975 | Hirdler | 544/190 |
| 4,024,140 | 5/1977 | Wojtowicz | 544/190 |

*Primary Examiner*—John M. Ford

[57] ABSTRACT

Alkali metal dichloroisocyanurates are instantly and quantitatively prepared by reacting cyanuric acid with an alkali metal hypochlorite in an aqueous reaction medium having a cyanuric acid to alkali metal hypochlorite mole ratio of 1:2.0 to 2.2, a pH value of 6.5 to 11.0 and a temperature from 10° C. to 55° C.

12 Claims, No Drawings

CYANURIC ACID CHLORINATION WITH ALKALI METAL HYPOCHLORITE

CROSS-REFERENCE TO RELATED APPLICATION

This is a continuation-in-part of application Ser. No. 721,295, filed Sept. 8, 1976, now abandoned.

BACKGROUND OF THE INVENTION

This invention provides a novel process for chlorinating cyanuric acid to produce alkali metal dichloroisocyanurates without the concomitant formation of nitrogen trichloride or other chloroamines.

Dichloroisocyanurates are well-known materials which are widely used as a source of available chlorine in solid bleaching, sanitizing and detergent compositions. The sodium and potassium salts are the most widely used in laundering compositions because they are very soluble and easily removed by rinsing.

Exemplification of one prior art process producing sodium dichloroisocyanurate is disclosed in U.S. Pat. No. 3,035,056. In this process, sodium dichloroisocyanurate is produced by chlorination of trisodiumisocyanurate with gaseous chlorine which results in the production of both sodium dischloroisocyanurate and sodium chloride. In contrast, U.S. Pat. No. 3,035,057 produces potassium dichloroisocyanurate by reacting trichloroiocyanuric acid with tripotassium isocyanurate.

U.S. Pat. No. 3,083,144 discloses another process for producing sodium dichloroisocyanurate by chlorinating cyanuric acid with sufficient chlorine and sodium hypochlorite or sodium hydroxide to produce solid dischloroisocyanuric acid at a pH value of from 1.5 to 3.5 and at a temperature from 5° to 45° C. wherein the mole ratio of said alkali to cyanuric acid is from 1.90:1 to 2.1:1 in a first aqueous medium, and neutralizing the solid dichloroisocyanuric acid with sodium hydroxide in a second aqueous medium at a pH from 6 to 7 to form sodium dichloroisocyanurate dihydrate particles which are subsequently separated and dried.

While these processes are effective for producing sodium or potassium dichloroisocyanurates, they require carefully controlled procedures for carrying out the chlorination and neutralization reactions to maximize product yields as well as to minimize the production of dangerous said products, such as nitrogen trichloride. Slight changes in the amount of chlorinating material and/or the alkali necessary to carry out the reaction can cause rapid changes in pH values which changes often result in cyanuric acid ring degradation.

SUMMARY OF THE INVENTION

It has been unexpectedly discovered that alkali metal dichloroisocyanurates can be produced directly from cyanuric acid without the need for separate chlorination and neutralization reactions by mixing sufficient amounts of water, cyanuric acid and an alkali metal hypochlorite to form a reaction medium containing 6 to 20 weight % cyanuric acid and having a cyanuric acid to alkali metal hypochlorite mole ratio of 1:2.0 to 2.2 and a pH value of 6.5 to 11.0; maintaining the reaction medium at a temperature from 10° to 55° C. to form chlorinated isocyanurates; adjusting the pH value of the reaction medium to between 6.0 and 8.0 with a mineral acid solution to neutralize alkali metal hydroxides formed during the reaction; cooling the neutralized reaction medium to precipitate the alkali metal dichloroisocyanurate; and recovering the alkali metal dichloroisocyanurate crystals from the reaction medium.

The process of the invention permits the formation of alkali metal dichloroisocyanurates from cyanuric acid in a commercially simple and efficient manner with essentially no triazine ring decomposition and little or no nitrogen trichloride or other chloroamine formation. It also permits the quantitative recovery of alkali metal dichloroisocyanurates with exceptionally high purities in relatively short periods of time.

DESCRIPTION OF PREFERRED EMBODIMENTS

In the process of the invention, sufficient amounts of cyanuric acid are mixed with an alkali metal hypochlorite to form a 6 to 20 weight % cyanuric acid slurry based upon the weight of the reaction medium. The cyanuric acid employed is preferably purified cyanuric acid containing less than about 2% amino substituted triazine impurities, such as melamine, ammeline, ammelide, ammeline:ammelide complex, and cyanuric acid:melamine complex, and preferably contains less than 0.5% amino substituted triazine impurities. From a commercial standpoint, slurry concentrations below about 6 weight % are not economical in view of the small amount of material being treated. Slurry concentrations above 20 weight % are difficult to handle and accordingly are not advisable. Preferably, the slurry concentration is from 10 to 20 weight % based upon the weight of the reaction medium.

The cyanuric acid slurry is obtained by either mixing dry cyanuric acid and the alkali metal hypochlorite compound in water or mixing aqueous solutions or mixtures of one or both of these materials together.

The alkali metal hypochlorites employed in this invention either singly or in combination are preferably sodium hypochlorite, lithium hypocholorite and potassium hypochlorite, even though other equivalent hypochlorites may also be employed. Some of these latter hypochlorites include magnesium hypochlorite and calcium hypochlorite.

To achieve complete conversion of the cyanuric acid to the alkali metal dichloroisocyanurates, sufficient alkali metal hypochlorite must be added to completely N-chlorinate the triazine molecule. A mole ratio of cyanuric acid to alkali metal hypochlorite of 1:2.0 to 2.2 gives high yields of essentially pure alkali metal dichloroisocyanurates. Optimum results are obtained by employing a mole ratio of cyanuric acid to alkali metal hypochlorite of 1:2.0 to 2.05. Any stoichiometry less than that stated results in the undesirable formation of mixtures containing cyanuric acid and the alkali metal dichloroisocyanurates, which mixtures require extensive purification procedures to prepare substantially pure alkali metal dichloroisocyanurates.

The reaction medium is preferably maintained at a temperature from 10° to 55° C. Since this is a mildly exothermic reaction, temperature control of the reaction medium is easily achieved by conventional external cooling means. The best mode contemplated for practicing this invention, which provides the highest yields, is with reaction temperatures between 20° and 30° C. Since the residence time in the reactor required for the reaction to reach completion is extremely short, temperatures above 30° C. may be employed with little or no decomposition of the alkali metal dichloroisocyanurates.

Conversion of cyanuric acid into the alkali metal dichloroioscyanurate is effected at pH values from 6.5 to 11.0 with maximum conversions being achieved at pH values between 6.5 and 8.0. Within these operating conditions, cyanuric acid is instantly and quantitatively converted to alkali metal dichloroisocyanurate. Since there is essentially no triazine ring decomposition, little or no nitrogen trichloride or other chloroamine by-products are formed.

Mixing of the cyanuric acid and alkali metal hypochlorites to form the resulting slurry as well as controlling the temperature of the reaction medium are achieved by conventional means and procedures. Mixing and temperature control may be done separately or carried out in a single stage, the latter being preferred since the reaction requires relatively short reaction times under operating conditions to instantly and quantitatively convert the cyanuric acid into alkali metal dichloroisocyanurates.

The reaction between cyanuric acid and the alkali metal hypochlorite is extremely rapid under operating conditions with complete conversions being achieved in a matter of seconds. High, commercially valuable yields are obtained with residence times in the reactor up to about 5 minutes and preferably up to about 2 minutes. These reaction times can be achieved with conventional reactors. The combination of high yields, short residence times and the ability to operate with a single stage process results in a commercial process which can employ a single, small, pipe-like reactor with high through-put. A pipe reactor is an elongated tubular reaction chamber wherein the feed enters the reactor in one end and product exits out of the other end. The reaction takes place within the tube which is heated by external sources. Use of pipe reactors eliminates most of the heat removal and operating problems of the prior art processes and results in a substantial reduction in the amount of capital equipment needed.

When the reaction is complete, the pH value of the reaction medium must be adjusted to between 6.0 and 8.0, and preferably between 6.5 and 7.5. If the pH value of the reaction medium were permitted to remain at pH values above about 10.0 for any substantial period of time following the reaction, which pH values form during the reaction, ring degradation substantially increases. The addition of a mineral acid to the reaction medium aids in lowering the pH value of the aqueous medium to the optimum equilibrium value of the alkali metal dichloroisocyanurate and neutralizes the alkali metal hydroxide formed during the reaction. The mineral acid is preferably employed as a dilute mineral acid solution containing from 20% to 60% by weight mineral acid dispersed in water. Mineral acid concentrations above 60% by weight should not be employed since these concentrations may cause an exothermic acidification reaction which converts the alkali metal dichloroisocyanurate into dichloroisocyanuric acid. Mineral acid concentrations below about 20% are not preferred since they introduce large quantities of water during neutralization which decreases process efficiency and increases the quantities of water that must be processed. Any mineral acid which is compatible with the reactants in the system may be employed, with preferred mineral acids being selected from the group consisting of sulfuric acid, phosphoric acid, nitric acid and hydrochloric acid, with sulfuric acid being most preferred.

When employing sodium hypochlorite as the alkali metal hypochlorite, the following theoretical chemical reactions occur:

$$C_3N_3O_3H_3 + 2NaOCl \rightleftharpoons NaC_3N_3O_3Cl_2 + NaOH + H_2O$$

$$NaOH + HX \rightleftharpoons NaX + H_2O$$

Following neutralization, the reaction medium is cooled by conventional means to precipitate additional alkali metal dichloroisocyanurate crystals. Preferably, the reaction medium is rapidly cooled in less than about 30 minutes to below about 20° C. and preferably to below about 10° C. Cooling is essential to prevent ring degradation and to lower the solubility of the alkali metal dichloroisocyanurate in the reaction medium. The precipitated crystals are recovered from the reaction medium by conventional liquid-solid separatory means.

The recovered crystals may then be optionally dried and stored. Drying may be carried out in any conventional manner to remove residual moisture and to produce a free-flowing crystalline product. These procedures are well known in the art and do not constitute a part of the invention.

The invention will be better understood from a consideration of the following examples. The examples are given to illustrate the invention, and are not deemed to be limiting thereof. All percentages given are based on weight unless otherwise indicated.

EXAMPLE I

Run 1

A 6.45 gram (0.05 mole) sample of purified cyanuric acid assaying 99.8% cyanuric acid was added to 54.6 grams of an aqueous solution containing 7.44 grams (0.10 mole) of sodium hypochlorite such that the reaction medium contained 10.56 weight % cyanuric acid. The aqueous reaction medium had a pH value of 8.6 and a temperature of 24° C. The cyanuric acid went into solution almost immediately upon its addition to the hypochlorite solution. The reaction medium pH value rose to 10.1 and the temperature rose to and was maintained at 26°–27° C. for 30 seconds. After 30 seconds, the reaction medium pH value was adjusted to 6.5 to 7.0 by addition of small amounts of dilute sulfuric acid whereupon the reaction vessel was quenched in an ice bath and cooled to 10° C. within two minutes. The reaction vessel was removed from the ice bath and the crystallized precipitate was filtered, washed and dried at 40° C. to remove surface water. The precipitate was identified as pure sodium dichloroisocyanurate dihydrate. The total yield was 12.8 grams which is equivalent to 100% recovery based on starting triazines.

EXAMPLE II

Runs 2 to 13

The procedure of Example I was repeated except that the process conditions were modified according to Table I. In all runs, the reaction temperature was maintained at 27° C. and the cyanuric acid to sodium hypochlorite mole ratio was 1:2.0. The results are set forth in Table I.

The results demonstrate that at reaction pH values from 6.5 to 8.0, essentially quantitative yields are obtained over the reaction time periods.

EXAMPLE III

Runs 14 to 19,

Comparative Runs A & B

The procedure of Example I was repeated except that the process conditions were modified according to Table II.

Runs 14 to 19 demonstrate that complete conversion of cyanuric acid is achieved by employing stoichiometric amounts of sodium hypochlorite. When less than stoichiometric amounts are employed, the degree of chlorination is drastically altered as demonstrated in Comparative Runs A and B. Runs 14 and 15 demonstrate that longer reaction times at elevated temperatures result in reduced triazine recoveries.

EXAMPLE IV

Runs 20 and 21

The procedure of Example I was repeated except that potassium hypochlorite (Run 20) and lithium hypochlorite (Run 21) were employed for sodium hypochlorite. The results are set forth in Table III.

The invention being thus described, it will be obvious that the same may be varied in many ways. Such variations are not to be regarded as a departure from the spirit and scope of the invention, and all such modifications are intended to be included within the scope of the following claims.

TABLE I

| Run # | Time (Min) | Reaction pH | % Triazine Recovery | Product |
|---|---|---|---|---|
| 2 | 0.5 | 6.5 | 99.9 | Pure sodium dichloroisocyanurate dihydrate |
| 3 | 5.0 | 6.5 | 99.9 | Pure sodium dichloroisocyanurate dihydrate |
| 4 | 10.0 | 6.5 | 99.9 | Pure sodium dichloroisocyanurate dihydrate |
| 5 | 15.0 | 6.5 | 99.9 | Pure sodium dichloroisocyanurate dihydrate |
| 6 | 0.5 | 7.5 | 99.9 | Pure sodium dichloroisocyanurate dihydrate |
| 7 | 5.0 | 7.5 | 99.9 | Pure sodium dichloroisocyanurate dihydrate |
| 8 | 10.0 | 7.5 | 99.9 | Pure sodium dichloroisocyanurate dihydrate |
| 9 | 0.5 | 8.3 | 99.9 | Pure sodium dichloroisocyanurate dihydrate |
| 10 | 5.0 | 8.3 | 99.9 | Pure sodium dichloroisocyanurate dihydrate |
| 11 | 10.0 | 8.3 | 99.9 | Pure sodium dichloroisocyanurate dihydrate |
| 12 | 0.5 | 10.5 | 99.5 | Pure sodium dichloroisocyanurate dihydrate |
| 13 | 5.0 | 10.5 | 91.5 | Pure sodium dichloroisocyanurate dihydrate |

TABLE II

| Run # | Initial CA* Conc % | Reaction Temp °C. | Final Adjusted pH | Reaction Time (Sec) | Cyanuric acid/ NaOCl Mole Ratio | % Triazine Recovery | Remarks |
|---|---|---|---|---|---|---|---|
| 14 | 9.8 | 43 | 6.8 | 30 | 1/2 | 99.9 | Product isolated as sodium dichloroisocyanurate dihydrate |
| 15 | 9.8 | 43 | 6.8 | 90 | 1/2 | 93.0 | Product isolated as sodium dichloroisocyanurate dihydrate |
| 16 | 11.5 | 27 | 7.0 | 30 | 1/2 | 99.9 | Product isolated as sodium dichloroisocyanurate dihydrate |
| 17 | 11.5 | 27 | 6.8 | 60 | 1/2 | 99.7 | Product isolated as sodium dichloroisocyanurate dihydrate |
| 18 | 11.5 | 27 | 6.8 | 300 | 1/2 | 99.6 | Product isolated as sodium dichloroisocyanurate dihydrate |
| 19 | 9.8 | 27 | 6.8 | 30 | 1/2 | 99.9 | Product isolated as sodium dichloroisocyanurate dihydrate |
| Comp.A | 9.8 | 27 | 6.8 | 30 | 1/1 | 99.9 | 51.8% conversion of CA* to sodium dichloroisocyanurate dihydrate |
| Comp.B | 9.8 | 27 | 6.8 | 30 | 1/1.5 | 98.9 | 75.8% conversion of CA* to sodium dichloroisocyanurate dihydrate |

*Cyanuric Acid

TABLE III

| Run # | Initial CA* Conc % | Rx Temp °C. | Final Rx pH | CA/** MOCl Ratio | % Triazine Recovery | Product |
|---|---|---|---|---|---|---|
| 20 | 8.9 | 27 | 6.8 | 1/2 | 99.9 | Potassium dichloroisocyanurate |
| 21 | 13.0 | 28 | 6.8 | 1/2 | 98.9 | Lithium dichloroisocyanurate |

*Cyanuric acid
**Cyanuric acid to alkali metal hypochlorite mole ratio

What is claimed is:

1. A process for producing an alkali metal dichloroisocyanurate, which comprises:
   (a) mixing sufficient amounts of water, cyanuric acid and an alkali metal hypochlorite to form a reaction medium containing 6 to 20 weight % cyanuric acid and having a cyanuric acid to alkali metal hypochlorite mole ratio of 1:2.0 to 2.2 and a pH value of 6.5 to 11.0;

(b) maintaining the reaction medium at a temperature from 10° to 55° C. to form chlorinated isocyanurates;

(c) adjusting the pH value of the reaction medium to between 6.0 and 8.0 with a mineral acid solution to neutralize alkali metal hydroxides formed during the reaction;

(d) cooling the neutralized reaction medium to precipitate the alkali metal dichloroisocyanurate; and (e) recovering the alkali metal dichloroisocyanurate crystals from the reaction medium.

2. The process of claim 1 wherein the alkali metal hypochlorites are selected from the group consisting of sodium hypochlorite, lithium hypochlorite and potassium hypochlorite.

3. The process of claim 1 wherein the reaction medium of step (a) contains 10 to 12 weight % cyanuric acid.

4. The process of claim 1 wherein the cyanuric acid to alkali metal hypochlorite mole ratio is 1:2.0 to 2.05.

5. The process of claim 1 wherein the pH value of step (a) is maintained between 6.5 and 8.0.

6. The process of claim 1 wherein the temperature of the reaction medium in step (b) is maintained between 20° and 30° C.

7. The process of claim 1 wherein the alkali metal hypochlorite is sodium hypochlorite and the alkali metal dichloroisocyanurate is sodium dichloroisocyanurate dihydrate.

8. The process of claim 1 wherein the alkali metal hypochlorite is lithium hypochlorite and the alkali metal dichloroisocyanurate is lithium dichloroisocyanurate.

9. The process of claim 1 wherein the alkali metal hypochlorite is potassium hypochlorite and the alkali metal dichloroisocyanurate is potassium dichloroisocyanurate.

10. The process of claim 1 wherein mixing step (a) and temperature maintenance step (b) are carried out in a single stage.

11. The process of claim 1 wherein the pH value of the reaction medium in step (c) is adjusted to between 6.5 and 7.5 with a mineral acid.

12. A process for producing sodium dichloroisocyanurate dihydrate which comprises:

(a) mixing sufficient amounts of water, cyanuric acid and sodium hypochlorite to form a reaction medium containing 10 to 12 weight % cyanuric acid and having a cyanuric acid to sodium hypochlorite mole ratio of 1:2.0 to 2.05 and a pH value of 6.5 to 8.0;

(b) maintaining the reaction medium at a temperature between 20° to 30° C. to form sodium dichloroisocyanurate;

(c) adjusting the pH value of the reaction medium to between 6.5 and 7.5 with a mineral acid solution to neutralize the sodium hydroxide formed during the reaction;

(d) cooling the neutralized reaction medium to precipitate the sodium dichloroisocyanurate dihydrate; and (e) recovering the sodium dichloroisocyanurate dihydrate crystals from the reaction medium.

* * * * *

UNITED STATES PATENT AND TRADEMARK OFFICE
CERTIFICATE OF CORRECTION

PATENT NO. : 4,208,519

DATED : June 17, 1980

INVENTOR(S) : Sidney Berkowitz

It is certified that error appears in the above—identified patent and that said Letters Patent is hereby corrected as shown below:

Column 1, line 31, "3,083,144" should read --3,803,144--.

Signed and Sealed this

Second Day of September 1980

[SEAL]

Attest:

SIDNEY A. DIAMOND

Attesting Officer

Commissioner of Patents and Trademarks